United States Patent [19]

Kleiner

[11] Patent Number: 4,521,347

[45] Date of Patent: Jun. 4, 1985

[54] PROCESS FOR PREPARING CHLOROPHENYLPHOSPHANES

[75] Inventor: Hans-Jerg Kleiner, Kronberg, Fed. Rep. of Germany

[73] Assignee: Hoechst Aktiengesellschaft, Frankfurt, Fed. Rep. of Germany

[21] Appl. No.: 489,813

[22] Filed: Apr. 29, 1983

[30] Foreign Application Priority Data

May 3, 1982 [DE] Fed. Rep. of Germany ....... 3216381

[51] Int. Cl.$^3$ ............................................... C07F 9/52
[52] U.S. Cl. .................................................. 260/543 P
[58] Field of Search ..................................... 260/543 P

[56] References Cited

PUBLICATIONS

Rozinov, Zh. Obsh. Khim, vol. 39, p. 712 (1969), p. 677 of English edition.
Petrov, K. A. et al., Derwent Abstract 83-51340K/21, (Abstract of Russian Pat. 943,243).
"Liebigs Analen der Chemie", 229, pp. 295 et seq. (1885) by Michaelis and von Soden.

*Primary Examiner*—Natalie Trousof
*Assistant Examiner*—L. Hendriksen
*Attorney, Agent, or Firm*—Curtis, Morris & Safford

[57] ABSTRACT

Chlorophenylphosphanes of the formula $$(C_6H_5)_nPCl_{3-n}$$

in which n=1 or 2, are prepared by reacting triphenylphosphane, $(C_6H_5)_3P$, with phosphorus trichloride, $PCl_3$, at temperatures between about 320° and 700° C.; in the temperature range between about 320° and 500° C. the reaction is preferably carried out under elevated pressure, in particular under autogenous pressure, while in the temperature range between about 500° and 700° C. atmospheric pressure is preferably used. The composition of the final product can be controlled by the choice of the molar ratio of the starting materials.

The final products dichlorophenylphosphane and chlorodiphenylphosphane are mainly intermediates in various fields, such as, for example, the crop protection and the polymer sectors.

7 Claims, No Drawings

PROCESS FOR PREPARING CHLOROPHENYLPHOSPHANES

For the purposes of the present invention, chlorophenylphosphanes are the two compounds dichlorophenylphosphane $C_6H_5PCl_2$ and chlorodiphenylphosphane $(C_6H_5)_2PCl$ which are encompassed by the general formula $(C_6H_5)_nPCl_{3-n}$ in which n=1 or 2.

They are in the main valuable intermediates in various fields, such as, for example, the crop protection and the polymer sectors.

For instance, crop protection agents are obtained—starting from dichlorophenylphosphane—via phenylthiophosphonyl dichloride, $C_6H_5P(S)Cl_2$. By using dichlorophenylphosphane as a starting material it is also possible to obtain in a known manner, for example, benzenephosphonous acid, $C_6H_5P(O)(OH)H$, which is of considerable economic importance for its use as such or in the form of its salts as a stabilizer for polyamides. Starting from chlorodiphenylphosphane, it is possible, via the corresponding diphenylphosphinates, $(C_6H_5)_2POR$ (R=an organic radical), to prepare, for example, acylphosphane oxide compounds, which are suitable for use as photoinitiators for photopolymerizable materials (European Pat. No. 7,508).

A number of different methods are known of preparing dichlorophenylphosphane and chlorodiphenylphosphane. K. Sommer describes an example of such a method on page 39 of Zeitschrift für Anorganische und Allgemeine Chemie, 376 (1970); the method consists in reacting triphenylphosphane, $(C_6H_5)_3P$, with phosphorus trichloride, $PCl_3$, under pressure at temperatures around 280° C., although the author does not provide any more detailed information concerning the pressure or, for example, the length of the reaction. It is said that when the starting materials are used in a ratio—presumably the molar ratio—of 1:1 they form roughly equal amounts—presumably equal molar amounts—of dichlorophenylphosphane and chlorodiphenylphosphane according to the equation $(C_6H_5)_3P + PCl_3 \rightarrow C_6H_5PCl_2 + (C_6H_5)_2PCl$.

Owing to their very different boiling points, the reaction products can be separated from each other by distillation. Under a pressure of about 26.6 Pa, the boiling point of dichlorophenylphosphane is 56° to 58° C., while that of chlorodiphenylphosphane is 115° to 120° C. If a small amount of aluminum chloride, $AlCl_3$, is added, the reaction described by K. Sommer is said to produce mainly dichlorophenylphosphane and only a small amount (less than 10%) of chlorodiphenylphosphane. It is said that dichlorophenylphosphane is obtained exclusively (besides unconsumed $PCl_3$) when the reaction (i.e. the reaction in the presence of $AlCl_3$) is carried out with the starting materials triphenylphosphane and phosphorus trichloride in a molar ratio of 1:3.

However, the use of $AlCl_3$ in this method constitutes something of a disadvantage.

Yet, without the addition of $AlCl_3$ virtually no reaction takes place, even in the presence of a considerable excess of phosphorus trichloride, as our own experiments (at about 280° C. under autogenous pressure and for a reaction time of about 6 hours) have demonstrated. If the molar ratio of the starting materials triphenylphosphane and phosphorus trichloride is about 1:4, the minute amount of reaction product obtained consists of about equal molar amounts of dichlorophenylphosphane and chlorodiphenylphosphane. The considerable excess of one of the reactants ($PCl_3$) thus appears here to have virtually no effect on the ratio of the two above-mentioned final compounds.

The absence observed in our experiments of a significant reaction between triphenylphosphane and phosphorus trichloride under the aforementioned conditions (about 280° C./autogenous pressure/a reaction period of about 6 hours) is incidentally in agreement with an earlier publication [page 303 of the paper by Michaelis and von Soden which starts on page 295 of Liebigs Annalen der Chemie 229 (1885)], according to which no chlorophenylphosphane was obtained on heating triphenylphosphane together with phosphorus trichloride at 290° to 310° C. in a sealed tube.

It is therefore an object of the present invention to provide conditions under which triphenylphosphane can be reacted with phosphorus trichloride—in the absence of a catalyst or the like—to give chlorophenylphosphanes in very high yields.

It has been found that this object is achieved, in a novel manner, by choosing a temperature which is higher than that given by K. Sommer and even higher than that given by Michaelis and von Soden, namely of about 320° to 700° C.

The invention accordingly relates to a process for preparing chlorophenylphosphanes of the formula $(C_6H_5)_nPCl_{3-n}$ in which n=1 or 2, by reacting triphenylphosphane, $(C_6H_5)_3P$, and phosphorus trichloride, $PCl_3$, at elevated temperature, which comprises carrying out the reaction at temperatures between about 320° and 700° C. In the lower temperature range, i.e. at about 320° to 500° C., the reaction is preferably carried out under elevated pressure, in particular under autogenous pressure, while in the upper temperature range, i.e. at about 500° to 700° C., atmospheric pressure is preferably used. This way of carrying out the process constantly achieves yields between about 60 and 90% of theory, while degrees of conversion are between about 70 and 95%; by means of an excess of one [$(C_6H_5)_3P$] or of the other ($PCl_3$) of the starting materials, this method furthermore permits one (chlorodiphenylphosphane) or the other (dichlorophenylphosphane) of the possible final products to be obtained in predominance.

These discoveries were very surprising, since it could not be assumed, on the basis of experimentation carried out in line with the publication by K. Sommer loc. cit. or on the basis of the earlier publication by Michaelis and von Soden loc. cit., that the reaction, which hardly proceeds at all at temperatures of about 280° to 310° C. in the absence of catalysts or the like, would now proceed in a very satisfactory manner at only slightly higher temperatures or higher (from about 320° C.) to give the desired products in substantial yields. Moreover, one had in fact to assume, on the basis of the publication by K. Sommer loc. cit. and the aforementioned experimentation, that to shift the ratio of the final products, dichlorophenylphosphane and chlorodiphenylphosphane, would require the addition of certain catalytically active substances, such as, for example, AlCl$_3$. Finally, it had to be thought more likely that at the relatively high temperatures used according to the invention, in particular at those above about 500° C., that at least the starting material triphenylphosphane would decompose rather than react with phosphorus trichloride, since, according to page 302 of the abovementioned article by Michaelis and von Soden in Liebigs Annalen der Chemie 229 (1885), triphenylphosphane began to decompose at as low a temperature as 360° C.

In the lower part of the temperature range of the process according to the invention, which extends from about 320° to 500° C., preferable temperatures are between about 340° and 400° C., in particular between about 350° and 370° C.

This version of the process is preferably also carried out under superatmospheric pressure, in particular under the pressure which becomes established in a sealed reaction vessel (i.e. the autogenous pressure) (generally between about 5 and 50 bar). The length of the reaction is here generally between about 10 minutes and 12 hours, the short reaction times being applicable at the higher temperatures, while the longer reaction times apply at the lower temperatures.

In the upper part of the temperature range of the process according to the invention, which extends from about 500° to 700° C., the preferred temperatures are between about 520° and 650° C., in particular between about 550° and 620° C.

This version of the process is preferably carried out under atmospheric pressure.

In this case, the length of reaction is virtually only on the order of seconds, where, again, the reaction times are longer in the case of the lower temperatures than for the higher temperatures.

The molar ratio of the starting materials triphenylphosphane and phosphorus trichloride can be varied within relatively wide limits. The preferable molar ratios are 1 to at least about 2 and at least about 2 to 1, because in these cases either dichlorophenylphosphane or chlorodiphenylphosphane is formed predominantly.

The equations underlying the reactions are:

Molar ratio of $(C_6H_5)_3P$ to $PCl_3 = 1$ to $\geqq 2$:

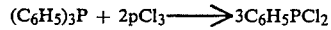

$(C_6H_5)_3P + 2PCl_3 \longrightarrow 3C_6H_5PCl_2$

Molar ratio of $(C_6H_5)_3P$ to $PCl_3 = \geqq 2$ to 1:

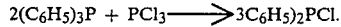

$2(C_6H_5)_3P + PCl_3 \longrightarrow 3(C_6H_5)_2PCl$.

Molar ratios of the two reactants of about 3–4 to 1 or 1 to about 3–4 are generally best; molar ratios of above about 5–7 to 1 or 1 to above about 5–7 usually yield no further benefit.

In particular in embodiments of the process performed at about 500° to 700° C. and atmospheric pressure the excess amounts of one of the reactants have a much less pronounced effect on the composition of the final product than in the case of embodiments of the process performed at about 320° to 500° C. and superatmospheric pressure; this is probably due to the short reaction times in embodiments of the process performed at about 500° to 700° C.

It is of course also possible to carry out the process according to the invention with the starting materials in a roughly equimolar ratio. However, in this case the result is then that neither of the two final products, dichlorophenylphosphane or chlorodiphenylphosphane, will be obtained in predominance; rather they are obtained in roughly equimolar amounts. The version of the process at about 320° to 500° C. is generally carried out by mixing triphenylphosphane and phosphorus trichloride which has been distilled as recently as possible in the appropriate molar ratio, and keeping the mixture, according to the temperature setting, for about 10 minutes to 12 hours in a suitable autoclave or pressure tube. When the reaction has ended, the reaction mixture is worked up by distillation. It is possible to carry out the process not only in a batchwise but also in a continuous manner.

When carrying out the process at about 500° to 700° C., the particular triphenylphosphane/phosphorus trichloride mixture is advantageously metered into a heated reaction zone with the aid of a metering device. An example of a suitable reaction zone is an electrically heated tube. On leaving the reaction zone, the reaction mixture collects in a receiving vessel, where it can be advantageous to apply cooling. The reaction material is then distilled.

It can be advantageous, in such embodiments of the process, to pass a gas stream through the reaction zone, suitable gases being inert gases, such as, for example, nitrogen or argon; but it is also possible to use, for example, hydrogen chloride. Embodiments of the process which are carried out at 500° to 700° C. are particularly suitable for continuous operation.

The process according to the invention always combines high degrees of conversion with high to very high yields of dichlorophenylphosphane and/or chlorodiphenylphosphane (relative to the starting compound used in the smaller amount). Owing to these high to very high yields combined with high degrees of conversion and owing to the fact that it is possible to react triphenylphosphane with phosphorus trichloride in the absence of any catalyst or the like to give predominantly one (dichlorophenylphosphane) or the other (chlorodiphenylphosphane) final product, the invention constitutes a considerable advance in this field.

The invention will now be illustrated in more detail by the examples which follow. The examples (of the invention) are followed by a comparative example concerning the state of the art as of K. Sommer, Zeitschrift für Anorganische und Allgemeine Chemie 376 (1970), page 39, which demonstrates that only a minute reaction of triphenylphosphane with phosphorus trichloride takes place at about 280° C. under autogenous pressure in the course of about 6 hours in the absence of a catalyst and that even a considerable excess of one of the reactants (PCl$_3$) has virtually no effect on the composition of the final product.

(A) VERSION OF THE PROCESS AT ABOUT 320°–500° C.

EXAMPLE 1

90 g (=0.3435 mole) of triphenylphosphane and 180 g (=1.309 moles) of freshly distilled phosphorus trichloride (→molar ratio of 1 to 3.81) are held at 350° C. for 3.5 hours in a 500 ml tantalum autoclave. During this period the pressure drops from 40 to 23 bar. The mixture is then distilled. This gives 137 g (=0.765 mole) of dichlorophenylphosphane (boiling point: 56°–58° C./26.6 Pa) and 25 g (=0.133 mole) of chlorodiphenylphosphane (boiling point: 115°–120° C./26.6 Pa; molar ratio of 5.75 to 1). The yield is 75% of theory in dichlorophenylphosphane and 22% of theory in chlorodiphenylphosphane, relative to the starting amount of triphenylphosphane. The excess phosphorus trichloride is collected in a cold trap upstream of the oil pump.

EXAMPLE 2

20 g (=0.076 mole) of triphenylphosphane and 30 g (=0.218 mole) of freshly distilled phosphorus trichloride (→molar ratio of 1 to 2.87) are held at 340°–350° C. for 5 hours in a 90 ml pressure tube. The mixture is then distilled. This gives 30 g (=0.17 mole) of dichlorophenylphosphane and 5 g (=0.0227 mole) of chlorodiphenylphosphane (molar ratio 7.5 to 1). The yield is 73% of theory in dichlorophenylphosphane and 20% of theory in chlorodiphenylphosphane, relative to the starting amount of triphenylphosphane. The excess phosphorus trichloride is collected in a cold trap upstream of the oil pump.

EXAMPLE 3

20 g (=0.076 mole) of triphenylphosphane and 21 g (=0.1527 mole) of freshly distilled phosphorus trichloride (→molar ratio of 1 to 2.0) are held at 340°–350° C. for 5 hours in a 90 ml pressure tube. The mixture is then distilled. This gives 23 g (=0.13 mole) of dichlorophenylphosphane and 8 g (=0.0363 mole) of chlorodiphenylphosphane (molar ratio 3.6 to 1). The yield is 56% of theory in dichlorophenylphosphane and 32% of theory in chlorodiphenylphosphane, relative to the starting amount of triphenylphosphane. The excess phosphorus trichloride is collected in a cold trap upstream of the oil pump.

EXAMPLE 4

213 g (=0.814 mole) of triphenylphosphane and 57 g (=0.414 mole) of freshly distilled phosphorus trichloride (→molar ratio of 1.97 to 1) are held at 350° C. for 6.5 hours in a 500 ml tantalum autoclave. The pressure is 7–10 bar. The mixture is then distilled. This gives 40 g of light ends which essentially consist of dichlorophenylphosphane, 175 g of chlorodiphenylphosphane and 34 g of triphenylphosphane. The chlorodiphenylphosphane yield is 78% of theory with a conversion of 84% of theory.

EXAMPLE 5

30 g (0.1145 mole) of triphenylphosphane and 16 g (0.116 mole) of freshly distilled phosphorus trichloride (→molar ratio of 1 to 1) are held at 350° C. for 6 hours in a 90 ml pressure tube. The mixture is then distilled. This gives 19 g (0.1065 mole) of dichlorophenylphosphane and 20 g (0.091 mole) of chlorodiphenylphosphane. The yield is 46.5% of theory in dichlorophenylphosphane and 40% of theory in chlorodiphenylphosphane.

(B) VERSION OF THE PROCESS AT ABOUT 500°–700° C.

EXAMPLE 6

A mixture of 46 g (=0.3345 mole) of freshly distilled phosphorus trichloride and 31 g (=0.1182 mole) of triphenylphosphane (→molar ratio of 2.83 to 1) is added dropwise in the course of 30 minutes to a slightly inclined 60 cm long quartz tube which is packed with quartz Raschig rings which have a diameter of 6 mm, is flushed with nitrogen, and is situated inside a hot electrical oven at 580° C. The reaction mixture which collects in the receiving flask is distilled. This gives 27 g (=0.151 mole) of dichlorophenylphosphane and 13.5 g (=0.0612 mole) of chlorodiphenylphosphane (→molar ratio of 2.5 to 1), unconverted phosphorus trichloride and unconverted triphenylphosphane. The yield relative to the starting amount of triphenylphosphane is 50% of theory in dichlorophophenylphosphane and 41% of theory in chlorodiphenylphosphane, with an 85% conversion.

EXAMPLE 7

A mixture of 60 g (=0.4364 mole) of freshly distilled phosphorus trichloride and 40 g (=0.1527 mole) of triphenylphosphane (→molar ratio of 2.86 to 1) is added dropwise in the course of 30 minutes to the apparatus which has been described in Example 6 and which is at 620° C. The subsequent distillation gives 38 g (=0.1212 mole) of dichlorophenylphosphane and 16.5 g (0.075 mole) of chlorodiphenylphosphane (→molar ratio of 2.83 to 1), unconverted phosphorus trichloride and unconverted triphenylphosphane. The yield relative to the starting amount of triphenylphosphane is 52% of theory in dichlorophenylphosphane and 38% of theory in chlorodiphenylphosphane, with an 87% conversion.

EXAMPLE 8

A mixture of 78 g (=0.567 mole) of freshly distilled phosphorus trichloride and 32 g (=0.122 mole) of triphenylphosphane (→molar ratio of 4.65 to 1) is added dropwise in the course of 35 minutes to the apparatus which has been described in Example 6 and which is at 620° C. The subsequent distillation gives 33 g (=0.184 mole) of dichlorophenylphosphane and 12 g (=0.0544 mole) of chlorodiphenylphosphane (→molar ratio 3.39 to 1), unconverted phosphorus trichloride and unconverted triphenylphosphane. The yield relative to the starting amount of triphenylphosphane is 55% of theory in dichlorophenylphosphane and 33% of theory in chlorodiphenylphosphane, with a 92% conversion.

EXAMPLE 9

A mixture of 120 g (=0.873 mole) of freshly distilled phosphorus trichloride and 80 g (0.3053 mole) of triphenylphosphane (→molar ratio 2.86 to 1) is added dropwise in the course of 30 minutes to the apparatus which has been described in Example 6 and which is at 620° C. The subsequent distillation gives 56 g (=0.313 mole) of dichlorophenylphosphane and 33 g (=0.15 mole) of chlorodiphenylphosphane (→molar ratio 2.08 to 1), unconverted phosphorus trichloride and unconverted triphenylphosphane. The yield relative to the starting amount of triphenylphosphane is 48% of theory in dichlorophenylphosphane and 46.5% of theory in chlorodiphenylphosphane, with a 71% conversion.

EXAMPLE 10

A mixture of 60 g (=0.4364 mole) of freshly distilled phosphorus trichloride and 40 g (=0.1527 mole) of triphenylphosphane (→molar ratio 2.86 to 1) is added dropwise in the course of 20 minutes to the apparatus which has been described in Example 6 and which is at 620° C. The subsequent distillation gives 24 g (=0.134 mole) of dichlorophenylphosphane and 17 g (=0.077 mole) of chlorodiphenylphosphane (→molar ratio 1.74 to 1), unconverted phosphorus trichloride and unconverted triphenylphosphane. The yield relative to the starting amount of triphenylphosphane is 41% of theory in dichlorophenylphosphane and 47% of theory in chlorodiphenylphosphane, with a 71% conversion. The chlorophosphanes obtained are particularly pure.

(C) COMPARATIVE EXAMPLE 20 g (=0.076 mole) of triphenylphosphane and 40 g (=0.291 mole) of freshly distilled phosphorus trichloride (→molar ratio of 1 to 3.82) are held at 280° C. for 6 hours in a sealed tube which has a volume of about 90 ml. The mixture is then distilled. This gives, besides unconverted triphenylphosphane and phosphorus trichloride, about 300 mg (=1.68 mmoles) of dichlorophenylphosphane and about 350 mg (=1.59 mmoles) of chlorodiphenylphosphane (→molar ratio of 1.06 to 1; weights on the basis of an analysis of the crude distillate by gas chromatography). The conversion in dichlorophenylphosphane and chlorodiphenylphosphane is about 2%.

I claim:

1. A process for preparing a chlorophenylphosphane of the formula $$(C_6H_5)_n PCl_{3-n}$$

in which n is 1 or 2, which comprises reacting triphenylphosphane and phosphorus trichloride in the absence of a catalyst at a temperature of from about 320° to 700° C.

2. A process as claimed in claim 1, wherein the reaction is carried out under atmospheric pressure at a temperature of from about 500° to 700° C.

3. A process as claimed in claim 2, wherein the starting materials triphenylphosphane and phosphorus trichloride are present in a molar ratio of 1 to about 3–4 or of about 3–4 to 1.

4. A process as claimed in claim 1, wherein the starting materials triphenylphosphane and phosphorus trichloride are present in a molar ratio of 1 to about 3–4 or of about 3–4 to 1.

5. A process as claimed in claim 1, wherein the reaction is carried out at elevated pressure and at a temperature of from 320° to 500° C.

6. A process as claimed in claim 5, wherein said elevated pressure is autogenous.

7. A process as claimed in claim 5, wherein the starting materials triphenylphosphane and phosphorus trichloride are present in a molar ratio of 1 to about 3–4 or of about 3–4 to 1.

* * * * *